United States Patent [19]

Miyake et al.

[11] Patent Number: 4,725,592
[45] Date of Patent: Feb. 16, 1988

[54] 1-ACYLOXYALKYL ESTERS OF CEPHALOSPORIN

[75] Inventors: Akio Miyake; Masayoshi Yamaoka; Mitsuo Numata, all of Osaka, Japan

[73] Assignee: Takeda Chemical Industries, Ltd., Osaka, Japan

[21] Appl. No.: 637,138

[22] Filed: Aug. 3, 1984

[30] Foreign Application Priority Data

Aug. 10, 1983 [JP] Japan ................. 58-147059

[51] Int. Cl.$^4$ ................... A61K 31/545; C07D 501/56
[52] U.S. Cl. ..................................... 514/206; 540/227
[58] Field of Search .................... 424/246; 544/27; 540/227; 514/206

[56] References Cited

U.S. PATENT DOCUMENTS

| 4,080,498 | 3/1978 | Numata et al. | 544/27 |
| 4,189,479 | 2/1980 | Kakeya et al. | 544/27 |
| 4,497,809 | 2/1985 | Yoshimura et al. | 514/206 |

OTHER PUBLICATIONS

Takahashi, et al., Chem. Abstracts, 78, (1973), Entry 111337v.
Takahashi, et al., Chem. Abstracts, 78, (1973), Entry 124613g.

Primary Examiner—Donald G. Daus
Assistant Examiner—William A. Teoli, Jr.
Attorney, Agent, or Firm—Antonelli, Terry & Wands

[57] ABSTRACT

A compound of the formula:

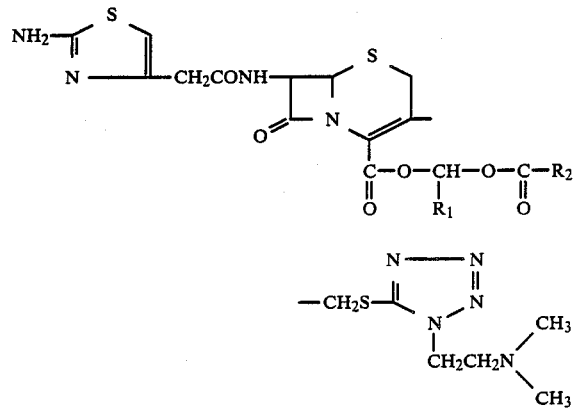

wherein $R_1$ stands for n-propyl or isopropyl; and $R_2$ stands for n-butyl, isobutyl, n-pentyl, n-hexyl or 2-ethylbutyl, or a pharmaceutically acceptable salt thereof, processes for preparing the same and a pharmaceutical composition thereof are provided. The compound can orally be applied as antibiotics having improved bioavailability.

5 Claims, No Drawings

1-ACYLOXYALKYL ESTERS OF CEPHALOSPORIN

This invention relates to compounds of the formula:

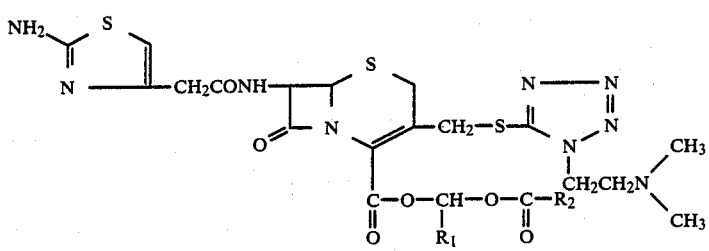

[I]

wherein $R_1$ stands for n-propyl on isopropyl; and $R_2$ stands for n-butyl, isobutyl, n-pentyl, n-hexyl or 2-ethylbutyl, or salts thereof.

For promoting the absorption, on oral administration, of 7β-[2-(2-aminothiazol-4-yl)acetamido]-3-[[[1-(2-dimethylaminoethyl)-1H-tetrazol-5-yl]thio]methyl]-ceph-3-em-4-carboxylic acid (this compound is described in U.S. Pat. No. 4,080,498; common name: cefotiam, hereinafter referred to briefly as compound [II]), it has been suggested to convert the carboxyl group at 4-position of the compound [II] into pivaloyloxymethyl ester, or a straight-chain or branched alkyl or alkoxycarbonyloxy-(substituted)alkyl ester(e.g., U.S. Pat. No. 4,189,479, EP No. 93548A and Japanese published unexamined patent application No. 77690/1982). However, these esters have still much to be desired in the respect of absorbability, stability, etc.

The present inventors conducted an intensive study of various ester derivatives of the compound [II], and found that, among α-(straight-chain or branched alkylcarbonyloxy group of 4–6 carbon atoms at the alkyl moiety)-substituted-butyl esters, the above novel compound [I] (referred to sometimes as the ester hereinafter) is efficiently absorbed from the gastrointestinal tract and, after absorption, quickly produces the compoun [II] in vivo to establish a high blood level of the compound [II] so that it is of value as an orally administrable broad-spectrum antibiotic displaying potent inhibitory effects not only against gram-positive and gram-negative bacteria but also against resistant strains thereof. It was also found that the salt of compound [I] has an improved water solubility and a better absorption efficiency compared with the ester, and facilitates the procedures of isolation, stabilization and processing into pharmaceutical preparations of the antibiotic.

Referring to the compound [I] of this invention, of n-propyl or isopropyl represented by $R_1$, is preferable the latter. Of n-butyl, isobutyl, n-pentyl, n-hexyl or 2-ethylbutyl, represented by $R_2$, is preferable n-butyl or isobutyl, and most preferable is isobutyl.

The compound [I] of this invention are shown as follows:
1-Pentanoyloxybutyl 7β-[2-(2-aminothiazo-4-yl)acetamido]-3-[[[1-(2-dimethylaminoethyl)-1H-tetrazol-5-yl]thio]methyl]ceph-3-em-4-carboxylate;
1-(3-Methylbutyryloxy)butyl 7β-[2-(2-amino-thiazol-4-yl)acetamido]-3-[[[1-(2-dimethylaminoethyl)-1H-tetrazol-5-yl]thio]methyl]ceph-3-em-4-carboxylate;
1-Hexanoyloxybutyl 7β-[2-(2-aminothiazol-4-yl)acetamido]-3-[[[1-(2-dimethylaminoethyl)-1H-tetrazol-5-yl]thio]methyl]ceph-3-em-4-carboxylate;
1-Heptanoyloxybutyl 7β-[2-(2-aminothiazol-4-yl)acetamido]-3-[[[1-(2-dimethylaminoethyl)-1H-tetrazol-5-yl]thio]methyl]ceph-3-em-4-carboxylate;
1-(3-Ethylpentanoyloxy)butyl 7β-[2-(2-aminothiazol-4-yl)acetamido]-3-[[[1-(2-dimethylaminoethyl)-1H-tetrazol-5-yl]thio]methyl]ceph-3-em-4-carboxylate;
1-Pentanoyloxy-2-methylpropyl 7β-[2-(2-aminothiazol-4-yl)acetamido]-3-[[[1-(2-dimethylaminoethyl)- 1H-tetrazol-5-yl]thio]methyl]ceph-3-em-4-carboxylate;
1-(3-Methylbutyryloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate;
1-Hexanoyloxy-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate;
1-Heptanoyloxy-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate; and
1-(3-Ethylpentanoyloxy)-2-methylpropyl 7β-[2-(2-aminothiazol-4-yl)acetamido]3-[[[1-2-dimethylaminoethyl)-1H-tetrazol-5-yl]thio]methyl]ceph-3-em-4-carboxylate.

Since the compound [I] is basic in itself, it can be converted into an acid addition salt thereof. Generally, 1 mole of the compound [I] forms an acid addition salt with 1 or 2 moles of an acid. Acids which are preferably employed for the formation of such acid addition salts include those known to form pharmaceutically acceptable salts with penicillins and cephalosporins; for example, inorganic acids such as hydrochloric acid, sulfuric acid or phosphoric acid; or organic acids such as maleic acid, acetic acid, citric acid, succinic acid, tartaric acid, malic acid, malonic acid, fumaric acid, benzoic acid, mandelic acid, ascorbic acid or methanesulfonic acid.

Preferred salts of the compound [I] are the monohydrochloride and dihydrochloride. The most desirable is the dihydrochloride.

The aminothiazole group of the compound [I] or a salt thereof may exist in the form of its tautomer i.e. iminothiazoline. As the compound [I] or a salt thereof has an asymmetric carbon in the carboxyl ester group at 4-position of the cephem nucleus, there exist two optically active forms (D-isomer and L-isomer). The compound [I] or a salt thereof can generally be used as a racemic compound but either the D-isomer or L-isomer or mixture of such optical isomers can also be employed. The compound [I] or a salt thereof is absorbed well through the gastrointestinal tract and after absorption the ester moiety at its 4-carboxyl position is promptly hydrolyzed with enzyme in the body to give the non-ester form of compound [I], which is the compound [II].

The compound [II]has strong antibacterial activity as mentioned in Antimicrobial Agent and Chemotherapy 14, 557–568 (1978). Thus, the compound [II] displays potent antibacterial activity against grampositive bacteria such as *Staphylococcus aureus*, and gram-negative bacteria such as *Escherichia coli, Klebsiella pneumoniae, Proteus vulgaris, Proteus mirabilis* or *Proteus morganii*.

Since the compound [I] or a salt thereof, when administered by the oral route, gives a high concentration of the compound [II] in the blood, it is effective in the treatment of infections due to said bacteria in man and other mammalian animals, such as respiratory tract or urinary tract infections due to said bacteria.

The compound [I] or a salt thereof is low in toxicity ($LD_{50}$ 3 g/kg, mice, p.o.) and can be orally administered. Therefore, in combination with per se known pharmaceutically acceptable excipients (e.g. starch, lactose, calcium carbonate, or calcium phosphate), binders (e.g. starch, gum arabic, carboxymethylcellulose, hydroxypropylcellulose or crystalline cellulose), lubricants (e.g. magnesium stearate or talc)or/and disintegrating agents (e.g. carboxymethylcalcium or talc), the compound [I] or a salt thereof can be formulated into dosage forms such as capsules, powders, fine granules, granules or tablets. It is also possible to add about 1 to 5 mole equivalents of a solid organic acid (e.g. citric acid, malic acid, tartaric acid, succinic acid, ascorbic acid or mandelic acid) to the compound [I] or a salt thereof and mold the mixture into granules in a conventional manner. Such granules can be further processed into capsules, tablets etc., by the established pharmaceutical procedures.

With regard to the dosage regimen, the compound [I] or a salt thereof can be administered at a daily dose of 0.3 to 5 g per adult human, preferably 0.5 to 3 g per adult human, divided into 3 or 4 equal doses.

The compound [I] or a salt thereof can be produced by per se known processes (for example, the processes described in U.S. Pat. No. 4,080,498, U.S. Pat. No. 4,189,479 or Japanese published unexamined patent application No. 77690/1982). Moreover, the compound [I] or a salt thereof can be produced by esterifying the compound [II] or a salt thereof with a compound of the formula:

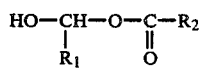

wherein $R_1$ and $R_2$ are of the same meaning as defined hereinbefore, or a reactive derivative thereof.

The reactive derivative is for example a compound of the formula:

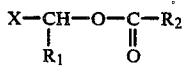

wherein X stands for a halogen; $R_1$ and $R_2$ are of the same meaning as defined hereinbefore.

Referring to the above formula [III], the halogen represented by X is for example chlorine, bromine or iodine. Of these species, X is preferably iodine for the purpose of esterification.

As the compound [III] has an asymmetric carbon atom, it can be optically resolved into D- and L-isomers by a per se known procedure and either of the isomers or a mixture thereof can be subjected to the contemplated esterification reaction.

The starting compound [II] can be subjected to the reaction in the form of an acid addition salt with an inorganic acid such as hydrochloric acid, sulfuric acid or nitric acid, or an organic acid such as oxalic acid or p-toluenesulfonic acid, or in the form of a salt with a base such as an alkali metal, e.g. sodium or potassium; alkaline earth metal, e.g. calcium or magnesium; or an organic amine, e.g. triethylamine, trimethylamine, pyridine, collidine or lutidine.

In conducting the esterification reaction, the starting compound [III] is used in a proportion of about 1 to 2 mole equivalents to each equivalent of the starting compound [II] or a salt thereof.

This reaction is generally carried out in a solvent inert to the reaction. Suitable species of such solvent include amides such as N, N-dimethylformamide (hereinafter referred to briefly as DMF), N, N-dimethylacetamide (hereinafter referred to briefly as DMAC) or hexamethylphosphorotriamide (hereinafter referred to briefly as HMPA); halogenated hydrocarbons such as dichloromethane or chloroform; sulfoxides such as dimethyl sulfoxide (hereinafter referred to briefly as DMSO) or sulfolane; ethers such as dioxane or tetrahydrofuran (hereinafter referred to briefly as THF); ketones such as acetone or methyl ethyl ketone; nitriles such as acetonitrile; liquefied sulfur dioxide, and so forth. Preferred are DMF, DMAC, HMPA, acetone, acetonitrile or liquefied sulfur dioxide. This esterification reaction is conducted generally at a temperature between about $-20°$ C. and $20°$ C. While the reaction can be conducted in the absence of a catalyst, a catalyst such as a phase transfer catalyst (e.g. 18-crown-6) can be employed. When liquefied sulfur dioxide is used as the solvent, the reaction is preferably conducted at a temperature near the boiling point $-10°$ C. of the solvent, i.e. about $-10°$ C. to $-20°$ C. The reaction time is generally about 10 minutes to 6 hours, depending on the species of reactants and solvent, etc.

The compound [I] or a salt thereof can also be produced by the following and other processes. Thus, a compound of the formula:

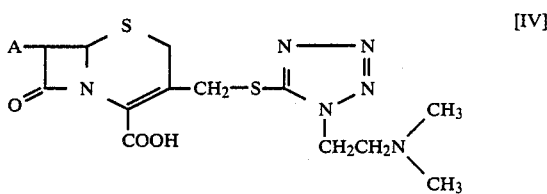

wherein A stands for an amino group or an acylamino group other than 2-(2-aminothiazol-4-yl)acetylamino, or a salt thereof is allowed to react with the compound [III] in the same manner as the above-described esterification reaction and when A is an acylamino group, the resulting ester is allowed to react with phosphorus pentachloride and, then, with alcohol (e.g. methanol, ethanol, propanol, isopropanol or n-butanol) [the process described in Journal of Medicinal Chemistry 18, 992 (1975), and West German Laid-open Patent Application Nos. 2460331 and 2460332]. The resulting compound of the formula:

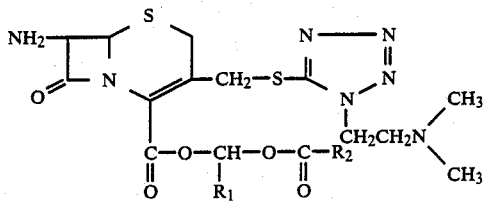

[V]

wherein symbols have the same meaning as defined hereinbefore, or a salt thereof is acylated with a compound of the formula:

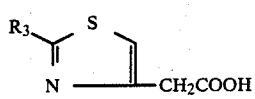

[VI]

wherein $R_3$ stands for an amino group or a protected amino group, or a reactive derivative thereof, if necessary followed by removing the protective group, to give the compound [I] or a salt thereof. The compound [IV] or a salt thereof can be produced according to the same procedure as described in e.g. U.S. Pat. Nos. 4,080,498 and 4,098,888.

Referring to the above formula [IV], when A is an acylamino group, the acyl group can be any of the acyl groups known per se in the field of cephalosporin compounds. Preferred species of such acylamino group are acetylamino, benzoylamino, phenylacetylamino, thienylacetylamino, phenyloxyacetylamino and 5-amino-5-carboxyvalerylamino (the substituent amino group may be protected with phthaloyl or the like). When A is an amino group or an amino-substituted acylamino group, the substituent amino group is preferably protected before the reaction and the protective group therefor may for example be per se known protective groups for an amino group, such as t-butoxycarbonyl, benzyloxycarbonyl, 2-hydroxy-1-naphthocarbonyl, trichloroethoxycarbonyl, 2-ethoxycarbonyl-1-methylvinyl, 2-methoxycarbonyl-1-methylvinyl, chloroacetyl, formyl, trifluoroacetyl or trityl.

The compound [IV] can be subjected to the reaction in the form of an acid addition salt with an inorganic acid such as hydrochloric acid, sulfuric acid or nitric acid, or an organic acid such as oxalic acid or p-toluenesulfonic acid, or in the form of a salt with a base such as an alkali metal, e.g. sodium or potassium; alkaline earth metal, e.g. calcium or magnesium; or an organic amine, e.g. triethylamine, trimethylamine, pyridine, collidine or lutidine.

The deacylation of the ester compound produced by allowing the compound [IV] (when A is an acylamino group) to react with the compound [III] is conducted in a per se known manner, using generally about 2 to 5 mole equivalents of phosphorus pentachloride and about 10 to 40 mole equivalents of alcohol per mole of the starting ester compound. This reaction is generally conducted in an inert solvent such as halogenated hydrocarbons, e.g. dichloromethane or chloroform. For the purpose of accelerating the reaction, a tertiary amine such as triethylamine, pyridine or N, N-dimethylaniline may be added to the reaction system. The reaction temperature is about −40° C. to about −20° C. The reaction time is usually about 1 hour.

When the resulting compound [V] or a salt thereof is allowed to react with the compound [VI] or a reactive derivative thereof, to produce the compound [I] or a salt thereof, the amino group of compound [VI] is preferably protected beforehand, and the protective group in the protected amino group represented by $R_3$ can be similar to the protective group for the amino group of the compound [IV]. The protected amino group represented by $R_3$ may be a group of the formula:

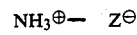

wherein $Z^\ominus$ is anion. The examples of anion represented by $Z^\ominus$ include halogen anion, sulfate anion etc. The halogen represented by Z is for example chlorine, bromine or iodine.

The compound [V] can be subjected to the reaction in the form of an acid addition salt with an inorganic acid such as hydrochloric acid, sulfuric acid or nitric acid, or an organic acid such as oxalic acid or p-toluenesulfonic acid. In this reaction, the compound [VI] may be used in the form of a reactive derivative. Thus, for example, it is subjected to said acylation reaction in the form of the corresponding acid halides, acid anhydrides, mixed acid anhydrides, active amides, active esters, etc. Preferred are active esters, the mixed acid anhydrides and acid halides. Examples of such active esters are p-nitrophenyl ester, 2,4-dinitrophenyl ester, pentachlorophenyl ester, N-hydroxyphthalimide ester and the ester formed by means of a Vilsmeier or similar reagent and so on. The mixed acid anhydrides are those with carbonic mono esters such as monomethyl carbonate or monoisobutyl carbonate, and those with lower alkanoic acids of 2 to 5 carbon atoms which may be substituted by halogens, such as pivalic acid or trichloroacetic acid. Examples of the acid halides are acid chloride, acid bromide etc. In this reaction, the compound [VI] or a reactive derivative thereof is used in a proportion of about 1 to 2 mole equivalents to each mole equivalent of the compound [V] or a salt thereof.

When the compound [VI] is used in the form of the free acid or a salt thereof, a suitable condensing agent is employed. Examples of such suitable condensing agent include N,N'-di-substituted carbodiimides such as N,N'-dicyclohexylcarbodiimide; azolides such as N,N'-carbonyl-imidazole or N,N'-thionyl-diimidazole; and dehydrating agents such as N-ethoxy-carbonyl-2-ethoxy-1, 2-dihydroquinoline, phosphorus oxychloride or alkoxyacetylenes (e.g. ethoxyacetylene) and so on. When the condensing agent is employed, the reaction appears to proceed via formation of a reactive derivative of the carboxylic acid.

Generally this reaction can be smoothly conducted in a solvent. Examples of the solvent include the common solvents which do not interfere with the contemplated reaction, such as water, acetone, diisobutyl ketone, THF, ethyl acetate, dioxane, acetonitrile, chloroform, dichloromethane, dichloroethylene, pyridine, dimethylaniline, DMF, DMAC or DMSO as well as mixtures of such solvents. While the reaction temperature is virtually optional, the reaction is generally conducted under cooling or at room temperature. When the reaction proceeds with liberation of an acid, a base is added to the reaction system as necessary. The base used for this purpose is examplified by aliphatic, aromatic or heterocyclic nitrogen-containing bases such as triethylamine, N,N-dimethylaniline, N-ethylmorpholine, pyridine, collidine or 2,6-lutidine; alkali metal carbonates such as sodium carbonate or potassium carbonate; alkali metal bicarbonate such as potassium hydrogen carbonate or sodium hydrogen carbonate. When the acylation reaction proceeds dehydratingly, it is preferable to remove water from the solvent. In some instances, the reaction is conducted under moisture-free conditions, e.g. in an inert gaseous atmosphere such as nitrogen gas. When the reaction product has a protective group, the protective group is removed by a per se known procedure (e.g. the procedure described in U.S. Pat. No. 4,080,498).

The compound [I] or a salt thereof can also be produced by the following procedure. Thus, the compound [V] is allowed to react with a 4-halogeno-3-oxobutyl halide, which is obtained by reacting diketene with a halogen (e.g. chlorine or bromine) in an equimolar ratio to give a compound of the formula:

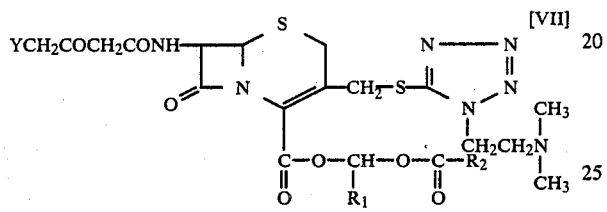

[VII]

wherein $R_1$ and $R_2$ have the same meaning as defined hereinbefore; and Y is a halogen, which is then allowed to react with thiourea. In the above formula [VII], the halogen represented by Y is for example chlorine or bromine.

The reaction of the compound [V] with 4-halogeno-3-oxobutyryl halide may be carried out by methods known per se e.g. the method disclosed in U.S. Pat. No. 4,080.498.

In reaction of the compound [VII] with thiourea, thiourea is preferably used as it is but may be used in the form of a salt with an alkali metal such as lithium, sodium or potassium, or ammonium salt. Generally the reaction is carried out using the two reactants in an equimolar ratio in a solvent and, in some instances, can be conducted in the presence of 1 to 2 molar equivalents of a base if necessary. Preferred examples of said solvent include water, methanol, ethanol, acetone, dioxane, acetonitrile, chloroform, ethylene dichloride , THF, ethyl acetate, DMF, DMAC and DMSO. Among these solvents, hydrophilic solvents can be used in admixture with water.

Preferred examples of said base include alkali metal hydroxides such as sodium hydroxide or potassium hydroxide; alkali metal carbonates such as sodium carbonate or potassium carbonate; alkali metal bicarbonates such as sodium hydrogen carbonate or potassium hydrogen carbonate and organic tertiary amines such as triethylamine, trimethylamine or pyridine. While there is virtually no limitation on the reaction temperature, generally the reaction is preferably conducted under cooling. The reaction generally proceeds at a fast rate and goes to completion within 10 minutes, although a reaction time in excess of 30 minutes is at times required. The compound [VII] can be easily produced by the above-described process. It can also be prepared by some other processes known per se.

The compound [I] or a salt thereof can also be produced by allowing a compound of the formula:

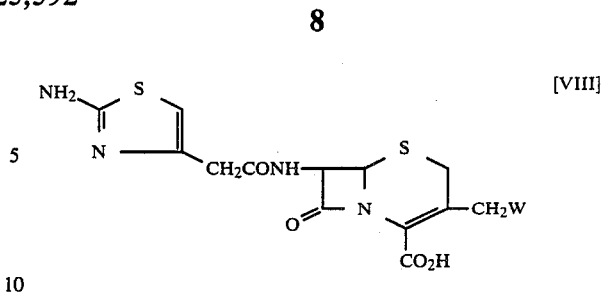

[VIII]

wherein W is acetoxy, acetoacetoxy, a halogen or carbamoyloxy, or a salt thereof to react with the compound [III] in the same manner as the esterification reaction described hereinbefore and allowing the resulting compound of the formula:

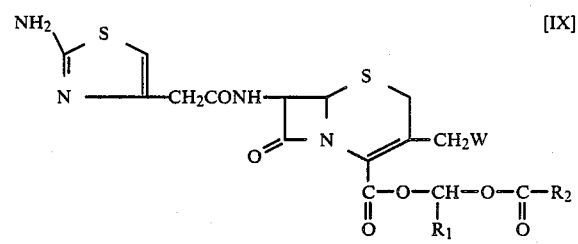

[IX]

wherein symbols have the same meanings as defined hereinbefore or a salt thereof to react with 1-(2-dimethylaminoethyl)-5-mercapto-1H-tetrazole. Referring to the above formulas [VIII] and [IX], the halogen represented by W is, for example, chlorine, bromine or iodine. The compound [VIII] or a salt thereof can be produced according to the same method as described in U.S. Pat. No. 4,080,498. The salt of compound [VIII] can be similar to that of compound [IV], and the salt of compound [IX] can be similar to that of compound [V]. In this reaction, the starting material 1-(2-dimethylaminoethyl)-5-mercapto-1H-tetrazole is used in an approximately equimolar proportion with respect to the compound [IX].

This reaction can generally be conducted smoothly in a solvent. Examples of such solvent include water, THF, ethyl acetate, dioxane, acetonitrile, chloroform, dichloromethane, DMF, DMAC and DMSO. When water is used, it can be used in admixture with a highly water-miscible solvent. Generally, this reaction is conducted in the presence of a base. Preferred examples of the base are weak bases such as alkali metal carbonates (e.g. sodium carbonate or potassium carbonate), or alkali metal bicarbonates (e.g. sodium hydrogen carbonate or potassium hydrogen carbonate). The base is used in an approximately equimolar proportion with respect to the starting compound, 1-(2-dimethylaminoethyl)5-mercapto-1H-tetrazole. While the reaction temperature is more or less optional, the reaction is generally conducted at room temperature up to 40° C. through 60° C. The reaction time is about 30 minutes to about 3 hours, depending on the solvent and the reaction temperature employed.

If the compound [I] or a salt thereof prepared as above contains its $\Delta^2$-isomer, the isomer can be converted to the compound [I] or a salt thereof by, for example, isomerizing the isomer to the $\Delta^3$-isomer by a per se known method [Journal of Medicinal Chemistry, Vol. 18, 986 (1975)], or converting the isomer to the $\Delta^3$-isomer via a corresponding S-oxide derivative and reducing it.

When the product compound [I] is produced in the form of free compound, it can be converted to a salt thereof by dissolving the free compound in an inert solvent such as dichloromethane or chloroform, and adding about 1 to 10 mole equivalents of the corresponding acid to the solution. When the compound [I] is produced in the form of an acid addition salt, it can be converted to the form of free base according to per se known procedures. When the compound [I] or a salt thereof is produced in the form of a racemic compound, it can be subjected to the optical resolution according to per se know procedures to isolate the optically active compounds (D- and L-isomers). The resulting compound [I] or a salt thereof can be isolated and purified by per se known procedures such as solvent extraction, pH adjustment, solvent transformation, crystallization, recrystallization and/or chromatography.

The starting compound [III] is produced by per se known processes. Further, the compound of the formula [III] wherein X stands for iodine, i.e. iodoalkyl acylate, can be produced by allowing an acid chloride [X] to react with an aldehyde derivative [XI] in the presence of a Lewis acid (first step of reaction) and then allowing the resulting chloroalkyl acylate i.e. the compound [III] wherein X stands for chlorine to react with sodium iodide (second step of reaction). (See the reaction formula below)

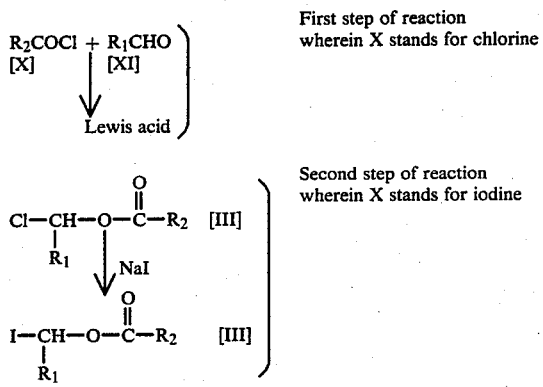

In the above formula, $R_1$ and $R_2$ are as defined hereinbefore. The compounds [X] and [XI] can be produced according to per se known methods.

The above first step of reaction is conducted in the presence of a Lewis acid such as anhydrous zinc chloride, aluminum chloride, tin chloride, etc. The reaction proceeds under cooling at about $-40°$ C. to $30°$ C., preferably at about $-40°$ C. to $0°$ C. or under heating at about $30°$ C. to $140°$ C., preferably at about $90°$ C. to $140°$ C. While the reaction time varies with the reaction temperature, it is generally about 1 to 3 hours under cooling and about 1 to 6 hours under heating. This reaction can proceed even in the absence of a solvent.

Following completion of the above first step of reaction, the reaction mixture is subjected to distillation, column chromatography, etc. to isolate the chloroalkyl acylate i.e. the compound [III] wherein X stands for chlorine. This compound is then allowed to react with sodium iodide to give the desired iodoalkyl acylates i.e. the compound [III] wherein X stands for iodine (second step of reaction). This second step of reaction is conducted in the presence of the common solvent such as acetone, acetonitrile, DMF, DMSO, etc. The reaction temperature may be room temperature or a slightly elevated temperature of about $40°$ C. to $50°$ C. The reaction time is about 15 minutes to 6 hours, preferably about 15 minutes to 2 hours.

The reaction product can be isolated and purified by per se known procedures such as solvent extraction, pH adjustment, distillation, distillation under reduced pressure, solvent-transformation and/or chromatography.

When the compound [X] is allowed to react with the compound [XI] the resulting compounds [III] (wherein X stands for choline or iodine) is produced in the form of racemic mixture.

The following Reference Examples, Examples and Experimental Examples are further illustrative but by no means limitative of this invention.

The symbols used in these Reference Examples and Examples have meanings defined below.

s: singlet; b.s.: broad singlet; d: doublet; d.d: double-doublet; t: triplet; q: quartet; m: multiplet.

REFERENCE EXAMPLE 1

1-Iodo-2-methylpropyl 3-methylbutyrate (a) To 250 g of 3-methylbutyrylchloride is added a catalytic amount of anhydrous zinc chloride. The mixture is cooled to $-20°$ C., to which is added dropwise 180 g of isobutyl aldehyde under stirring, followed by further stirring at the same temperature for one hour. Then, temperature of the reaction solution is reverted to $5°$ C., followed by further stirring for one hour. The reaction solution is subjected to a silicagel chromatography (Kiesel-gel ® 60, 230–400 mesh, E. Merck, W. Germany). Elution is conducted with 2 l of petroleum ether. The eluate is concentrated under reduced pressure. The concentrate is subjected to distillation under reduced pressure to give 311 g of 1-chloro-2-methylpropyl 3-methylbutyrate as colorless oil, b.p. $106°–108°$ C./32 mmHg.

IR $\nu_{max}^{liquid\ film}$ cm$^{-1}$: 1765, 1750.

NMR(CDCl$_3$)δ: 0.9(d,J=8 Hz,12H), 1.30–1.60(m,2H), 2.20(d,J=6 Hz,2H), 6.10(d,J=4 Hz,1H).

(b) In 200 ml of acetonitrile warmed to $60°$ C. is dissolved 35 g of sodium iodide. To the solution is added 12 g of 1-chloro-2-methylpropyl 3-methylbutyrate obtained in (a) above, and the mixture is stirred for 40 minutes. The reaction solution is added to 500 ml of ice-water, and the aqueous solution is subjected to extraction with hexane. The extract is washed with water, then further washed with 5% aqueous solution of sodium thiosulfate, followed by drying over anhydrous magnesium sulfate. Removal of the solvent by evaporation under reduced pressure gives 10 g of the first-mentioned compound.

IR $\nu_{max}^{liquid\ film}$ cm$^{-1}$: 1760, 1740.

After the manner similar to Reference Example 1, the following compounds are obtained:

1-Iodo-2-methylpropyl pentanoate
IR $\nu_{max}^{liquid\ film}$ cm$^{-1}$: 1760, 1740.
1-Iodo-2-methylpropyl hexanoate
IR $\nu_{max}^{liquid\ film}$ cm$^{-1}$: 1760, 1740.
1-Iodo-2-methylpropyl 3-ethylpentanoate
IR $\nu_{max}^{liquid\ film}$ cm$^{-1}$: 1760, 1740.
1-Iodobutyl 3-methylbutyrate
IR $\nu_{max}^{liquid\ film}$ cm$^{-1}$: 1760, 1740.
1-Iodobutyl pentanoate
IR $\nu_{max}^{liquid\ film}$ cm$^{-1}$: 1760, 1740.

EXAMPLE 1

1-(3-Methylbutyryloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 1)

In 120 ml of dimethylacetamide is dissolved 6.0 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate, and the solution is cooled to 2° C.

To thus cooled solution, while stirring, is added 10 g of 1-iodo-2-methylpropyl 3-methylbutyrate at one stroke, and the stirring is continued for seven minutes.

To the reaction solution is added 70 ml of 2N-ethereal hydrogen chloride, followed by further addition of 300 ml of ether. The ether layer is removed, and the remainder is dissolved in 50 ml of 1N-hydrochloric acid. The solution is subjected to a column-chromatography on XAD-II ® resin (manufactured by Rhom & Haas, Inc., U.S.A.), followed by elution with acetonitrilewater (1:4). The fractions containing the object compound are combined and subjected to evaporation under reduced pressure to remove the solvent, followed by lyophilizing to give 3.2 g of the above titled compound as colorless powder.

IR $\nu_{max}^{KBr}$ cm$^{-1}$: 1780, 1750, 1680.

NMR(d$_6$-DMSO)δ: 0.90(d,J=7.5 Hz,6H), 0.93(d,J=7.5 Hz,6H), 1.90-2.20(m,4H), 2.85(s,6H), 3.60(s,2H), 3.65-3.90(m,2H), 4.30 (s,2H), 4.76(t,J=6 Hz,2H), 5.10(d, J=4.5 Hz,1H), 5.60-5.80(m,1H), 6.63 (s,1H), 6.63-6.76(m,1H), 8.90-9.50 (b.s,1H), 9.20(d,J=9 Hz,1H).

Elemental Analysis for $C_{27}H_{39}N_9O_6S_3.2HCl.9/2-H_2O$: Calcd.(%): C,38.80; H,6.03; N,15.09. Found (%): C,38.72; H,5.62; N,15.08.

EXAMPLE 2

1-(3-Methylbutyryloxy)butyl 7β-[2-(2-aminothiazol-4-yl)acetamido]-3-[[[1-(2-dimethylaminoethyl) -1H-tetrazol-5-yl]thio]methyl]ceph-3-em-4-carboxylate dihydrochloride (Compound No. 2)

IR $\nu_{max}^{KBr}$ cm$^{-1}$: 1780, 1750, 1680.

NMR(d$_6$ -DMSO)δ: 0.80-0.95(m,9H), 1.35(q,J=6 Hz,2H), 1.70-2.10(m,4H), 2.20(s,2H), 2.90 (s,6H), 3.60(s,2H), 3.80-3.90(m,2H), 4.30(s,2H), 4.80(t,J=6 Hz,2H), 5.15 (d,J=4.5 Hz,1H), 5.60-5.80(m,1H), 6.65(s,1H), 6.70-7.00(m,1H), 9.00-9.70(b.s,1H), 9.25(d,J=9 Hz,1H).

Elemental Analysis for $C_{27}H_{39}N_9O_6S_3.2HCl.7/2-H_2O$: Calcd.(%): C,39.66; H,5.92; N,15.42. Found (%): C,39.57; H,5.46; N,15.76.

EXAMPLE 3

1-Pentanoyloxy-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No.3)

IR $\nu_{max}^{KBr}$ cm$^{-1}$: 1780, 1750, 1680.

NMR(d$_6$-DMSO)δ: 0.85-1.00(m,9H), 1.10-1.65(m,4H), 1.90-2.20(m,1H), 2.30-2.40(m,3H), 2.90(s,6H), 3.70(s,2H), 3.80-3.90 (m,2H), 4.40(s,2H), 4.70(t,J=6 Hz,2H), 5.20(d,J=6 Hz,1H), 5.60-5.80(m,1H), 6.65(s,1H), 6.70-6.90(m,1H), 9.20-9.80(b.s,1H), 9.35(d,J=9 Hz,1H).

Elemental Analysis for $C_{27}H_{39}N_9O_6S_3.2HCl.3H_2O$: Calcd.(%): C,40.10; H,5.86; N,15.59. Found (%): C,40.02; H,5.49; N,15.89.

EXAMPLE 4

1-Pentanoyloxybutyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 4)

IR $\nu_{max}^{KBr}$ cm$^{-1}$: 1780, 1750, 1680.

NMR(d$_6$-DMSO)δ: 0.75-1.00(m,6H), 1.10-1.95(m,8H), 2.30(t,J=6 Hz,2H), 2.80(s,6H), 3.60 (s,2H), 3.70-3.90(m,2H), 4.35(s,1H), 4.80(t,J=6 Hz,2H), 5.15(d,J=6 Hz,1H), 5.60-5.80(m,1H), 6.65(s,1H), 6.70-7.00(m,1H), 9.10-9.80(b.s,1H), 9.25 (d,J=9 Hz,1H).

Elemental Analysis for $C_{27}H_{39}N_9O_6S_3.2HCl.7/2-H_2O$: Calcd.(%): C,39.66; H,5.92; N,15.42. Found (%): C,39.61; H,5.50; N,15.64.

EXAMPLE 5

1-Heptanoyloxy-2-methylpropyl 7β-[2-(2-aminothiazol-4-yl)acetamido]-3-[[[1-(2-dimethylaminoethyl) -1H-tetrazol-5-yl]thio]methyl]ceph-3-em-4-carboxylate dihydrochloride (Compound No. 5)

IR $\nu_{max}^{KBr}$ cm$^{-1}$: 1780, 1750, 1680.

NMR(d$_6$-DMSO)δ: 0.90-1.05(m,9H), 1.20(s,6H), 1.50-1.70(m,2H), 2.20-2.50(m,2H), 2.90 (s,6H), 3.70(s,4H), 3.80-4.00(m, 1H), 4.30-4.50(m,3H), 4.85(t,J=6 Hz,2H), 5.20(d,J=6 Hz,1H), 6.70 (s,1H), 7.70-7.90(m,1H), 9.20-9.80 (b.s,1H), 9.30(d,J=9 Hz)

Elemental Analysis for $C_{29}H_{43}N_9O_6S_3.2HCl.2H_2O$: Calcd.(%): C,42.59; H,6.04; N,15.41. Found (%): C,42.33; H,5.90; N,15.38.

EXAMPLE 6

1-(3-Ethylpentanoyloxy)-2-methylpropyl 7β-[2-(2-aminothiazol-4-yl)acetamido]-3-[[[1-2-dimethylaminoethyl)-1H-tetrazol-5-yl]thio]methyl]ceph-3-em-4-carboxylate dihydrochloride (Compound No. 6)

IR $\nu_{max}^{KBr}$ cm$^{-1}$: 1780, 1750, 1680.

NMR(D$_2$O)δ: 0.97(t,J=7 Hz,12H), 1.13-1.55(m,4H), 1.55-1.88(m,1H), 1.88-2.20(m,1H), 2.41 (d,J=6 Hz,2H), 3.12(s,6H), 3.84(s,2H), 3.91(t,J=6 Hz,2H), 4.97(t,J=6 Hz,2H), 5.20 (d,J=5 Hz,1H), 5.73(d,J=5 Hz,1H), 6.66-6.80 (m,1H), 6.75(s,1H).

Elemental Analysis for $C_{29}H_{43}N_9O_6S_3.2HCl.3/2-H_2O$:

Calcd.(%): C,43.01; H,5.97; N,15.57.

Found (%): C,43.02; H,6.13; N,15.57.

EXAMPLE 7

1-(3-Methylbutyryloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 1)

(a) Production of 1-(3-methylbutyryloxy)-2-methylpropyl 7β-amino-3-[[[1-(2-dimethylaminoethyl)-1H-tetrazol-5-yl]thio]methyl]ceph-3-em-4-carboxylate dihydrochloride To 60 ml of dimethylformamide solution containing 4.22 g of 7β-amino-3-[[[1-(2-dimethylaminoethyl)-1H-tetrazol-5-yl]thio]methyl]ceph-3-em-4-carboxylic acid dihydrochloride is added 1.67 g of potassium acetate.

The mixture is cooled to 0° C. With stirring, 5.0 g of 1-iodo-2-methylpropyl 3-methylbutyrate is added dropwise to the solution, followed by stirring at 0° C. for 5 minutes. The reaction mixture is poured into a mixture of 60 ml of methylene chloride and 60 ml of 0.1N-HCl and the aqueous layer is separated. The aqueous solution is adjusted to pH 6.0 with a saturated aqueous sodium bicarbonate solution and extracted with methylene chloride. To the methylene chloride solution is added water and the mixture is adjusted to pH 2.0 with 4N-HCl. The aqueous layer is separated and lyophilized to obtain 3.0 g of the title compound.

IR $\nu_{max}^{nujol}$®cm$^{-1}$: 1780, 1750, 1670.

(b) Production of 1-(3-methylbutyryloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride To a mixture of 30 ml of water and 30 ml of methylene chloride is added 1.7 g of the compound obtained in the above (a), followed by addition of 0.55 g of sodium bicarbonate with stirring. The organic layer is separated and dried over anhydrous calcium chloride. After removal of the drying agent by filtration, is added to the filtrate a 20 ml of dimethylformamide solution containing 0.60 g of (2-aminothiazol-4-yl)acetic acid hydrochloride and 0.62 g of dicyclohexylcarbodiimide, followed by stirring the mixture at room temperature. The resulting precipitates are removed by filtration and 150 ml of ethyl acetate and 100 ml of ice cooled water are added to the filtrate. The organic layer is separated, washed with water and a saturated aqueous sodium chloride solution and is dried over anhydrous magnesium sulfate. After removal of drying agent by filtration, the filtrate is concentrated to 10 ml under reduced pressure, followed by addition of an anhydrous ethereal hydrogen chloride solution. The resulting precipitates are collected by filtration to obtain 0.3 g of white powder.

This product shows the same NMR and IR spectra as those of the product obtained in Example 1.

EXAMPLE 8

1-(3-Methylbutyryloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 1)

To a mixture of 15 ml of water and 15 ml of methylene chloride is added 1.1 g of 1-(3-methylbutyryloxy)-2-methylpropyl 7β-amino-3-[[[1-(2-dimethylaminoethyl)-1H-tetrazol-5-yl]ceph-3-em-4-carboxylate dihydrochloride obtained in Example 7 (a) and the mixture is stirred together with 0.30 g of sodium bicarbonate. The organic layer is separated and dried over anhydrous calcium chloride. Then, the solvent is distilled off under reduced pressure. The residue is dissolved in 15 ml of methylene chloride and the solution is cooled to −25° C. To this solution is added 2.0 ml of methylene chloride solution containing 0.5 g of 4-chloroacetoacetyl chloride and the mixture is stirred at −20° C. to −15° C. for 20 minutes. Then, 0.76 g of thiourea and 5 ml of dimethylacetamide are added and the mixture is stirred at room temperature for 3 hours. Water is added to the reaction mixture and the aqueous layer is separated. The aqueous solution is adjusted to pH 6.0 and extracted with methylene chloride. The methylene chloride layer is admixed with water and adjusted to pH 1.5 with 2N-HCl. The aqueous layer is separated and subjected to column chromatography on Amberlite XAD-II® (produced by Rohm & Haas Co., U.S.A.), elution being carried out with 120 ml of 0.1N-HCl and then with 20% acetonitrile-0.01N-HCl. The eluate is lyophilized to obtain 0.5 g of white powder. This product shows the same NMR and IR spectra as those of the product obtained in Example 1.

EXAMPLE 9

1-(3-Methylbulyryloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 1)

(a) Production of 1-(3-methylbutyryloxy)-2-methylpropyl 7β-[2-(2-aminothiazol-4-yl)acetamido]-3-acetoacetoxymethyl-ceph-3-em-4-carboxylate In 30 ml of N,N-dimethylformamide is dissolved 4.76 g of sodium 7β-[2-(2-aminothiazol-4-yl)acetamido]-3-acetoacetoxymethyl-ceph-3-em-4-carboxylate and the solution is cooled to −5° C. With stirring, 5.0 g of 1-iodo-2-methylpropyl 3-methylbutyrate is added dropwise, followed by stirring for further 5 minutes. Thereafter, following the procedupe of Example 1, 2.5 g of the title compound is obtained.

IR $\nu_{max}^{KBr}$ cm$^{-1}$: 1780, 1750, 1630.

NMR(d$_6$-DMSO)δ: 0.90(d,J=7.5 Hz,6H), 0.93(d,J=7.5 Hz,6H) 1.90–2.20(m,4H), 2.10(s,3H), 2.20–2.40 (m,1H), 3.60(s,2H), 3.60–3.70(m,2H), 4.76(t,J=6 Hz,2H), 5.10(d,J=4.5 Hz,1H), 5.70(d.d,J=4.5 Hz and 6 Hz,1H), 6.60(s, 1H), 6.63(d,J=4.5 Hz,1H), 9.0–9.6(b. s,1H), 9.20(d,J=6 Hz,1H).

(b) Production of 1-(3-methylbutyryloxy)-2-methylpropyl 7β-[2-(2-aminothiazol-4-yl)acetamido-3-[[[1-(2-dimethylaminoethyl)-1H-tetrazol-5-yl]thio]methyl]ceph-3-em-4-carboxylate dihydrochloride To 30 ml of an acetone solution containing 2.3 g of the compound obtained in the above (a) is added 10 ml of an aqueous solution containing 0.9 g of 1-(2-dimethylaminoethyl)-5-mercapto-1H-tetrazole and 0.8 g of sodium bicarbonate and the mixture is heated to 40° C. for one hour with stirring. The reaction mixture is poured into a mixture of 150 ml of ethyl acetate and 50 ml of ice water and the organic layer is separated. The organic layer is washed with ice water and then with saturated aqueous sodium chloride and dried over anhydrous magnesium sulfate. Thereafter, the solvent is distilled off under reduced pressure. The residue is dissolved in 5 ml of 0.01N-HCl and insoluble matter is removed by filtration. The filtrate is lyophilized to obtain 0.05 g of the title compound as white powder.

This product shows the same NMR and IR spectra as those of the product obtained in Example 1.

EXAMPLE 10

Compound No. 1 [338 g; 250 g in terms of the nonester (compound [II])] as obtained in Example 1 is evenly admixed with 70.5 g of hydroxypropylcellulose and 70.5 g of carboxymethylcellulose. The mixture is distributed in 264.5 mg (125 mg in terms of the nonester) into capsules in the conventional manner.

EXAMPLE 11

Compound No. 1 [338 g; 250 g in terms of the non-ester (Compound [II])] as obtained in Example 1 is evenly admixed with 70 g of starch and 6 g of hydroxypropylcellulose. The mixture is tableted in the conventional manner to provide 232 mg tablets (125 mg in terms of the non-ester).

Experimental Example

The compounds of Examples (compound Nos. 1 and 2) and, as a control compound, the pivaloyloxymethyl ester of compound [II] (hereinafter referred to briefly as compound A) are administered orally to mice, each compound to one animal, in the dose of 100 mg/kg in terms of the non-ester, i.e. compound [II]. At 0.25, 0.5, 1.0 and 2.0 hours after administration, the concentration of compound [II] in the plasma of the mouse is measured by the cup method using *Proteus mirabilis* Eb 313 as the test organism and the area under plasma concentration-time curve from zero to 2 hours (AUC) is calculated.

As a control, compound [II] is subcutaneously administered to a mouse and the AUC value is calculated as above. The bioavailability is calculated by means of the following equation.

$$\text{Bioavailability (\%)} = \frac{AUC\ (p.o.)}{AUC\ (s.c.)} \times 100$$

The results are shown in Table 1.

TABLE 1

| Compound No. | Plasma level of non-ester (Compound [II]) (μg/ml), n = 3* | | | | AUC μg. hr/ml | Bioavailability (%) |
|---|---|---|---|---|---|---|
| | 0.25 (hr) | 0.5 (hr) | 1.0 (hr) | 2 (hr) | | |
| 1 | 55.4 | 37.0 | 8.46 | 2.5 | 35.3 | 91.0 |
| 2 | 74.3 | 21.6 | 5.36 | 1.8 | 31.6 | 81.4 |
| A | 21.0 | 16.2 | 6.1 | 0.6 | 16.2 | 41.8 |
| Control: Subcutaneous Subcutaneous administration of Compound [II] | 69.2 | 29.0 | 13.2 | 1.5 | 38.8 | 100 |

*Average of the values obtained in three mice

We claim:

1. A compound of the formula:

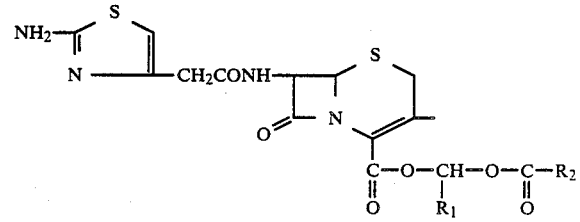

wherein $R_1$ represents n-propyl or isopropyl; and $R_2$ represents isobutyl; or a pharmaceutically acceptable salt thereof.

2. A compound according to claim 1, wherein the pharmaceutically acceptable salt is hydrochloride.

3. A compound according to claim 1, the compound of the formula being 1-(3-methylbutyryloxy)-2-methylpropyl 7β-[2-(2-aminothiazol-4-yl)acetamido]-3-[[[1-(2-dimethylaminoethyl)-1H-tetrazol-5H yl]thio]methyl]-ceph-3-em4carboxylate.

4. A compound according to claim 1, the compound of the formula being 1-(methylbutyryloxy)butyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

5. A pharmaceutical composition comprising a compound of the formula:

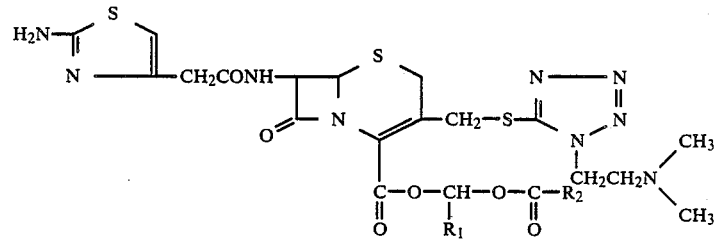

wherein $R_1$ represents n-propyl or isopropyl; and $R_2$ represents isobutyl; or a pharmaceutically acceptable salt thereof, as an effective ingredient.

* * * * *